US00PP29745P2

(12) United States Plant Patent
Hansen

(10) Patent No.: US PP29,745 P2
(45) Date of Patent: Oct. 9, 2018

(54) ***TIARELLA* PLANT NAMED 'CUTTING EDGE'**

(50) Latin Name: ***Tiarella* hybrid**
Varietal Denomination: Cutting Edge

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/932,132

(22) Filed: Feb. 7, 2018

(51) Int. Cl.
*A01H 5/02* (2018.01)
*A01H 6/80* (2018.01)

(52) U.S. Cl.
USPC ..... Plt./486
CPC ..... *A01H 6/80* (2018.05)

(58) Field of Classification Search
USPC ..... Plt./486
See application file for complete search history.

*Primary Examiner* — Annette H Para

(57) ABSTRACT

The new hybrid plant cultivar of *Tiarella* 'Cutting Edge' has pale pink flower buds developing into white flowers on moderately dense branched panicles in spring above a clumping mound of palmately-lobed leaves that have a large center burgundy palm chartreuse to medium green. Leaves are deeply dissected nearly to petiole with sharply acute lobe apices and toothed margin.

1 Drawing Sheet

Botanical denomination: *Tiarella* hybrid.
Cultivar designation: 'Cutting Edge'.

BACKGROUND OF THE INVENTION

The present invention relates to a new and distinct cultivar of foamflower in the Saxifragaceae family and given the cultivar name of 'Cutting Edge'. *Tiarella* 'Cutting Edge' resulted from a selfing of *Tiarella* 'Timbuktu' (not patented) as the female or seed parent and as the male or pollen parent. The new plant was hybridized by the inventor on Feb. 13, 2013, sown in the spring of 2013 and initially selected from among other seedlings growing at a nursery in Zeeland, Mich. in the summer of 2014 and ultimately given the breeder code 13-16-5. *Tiarella* 'Cutting Edge' has been asexually propagated by division and by careful shoot tip tissue culture propagation at the same nursery in Zeeland, Mich., and the resultant asexual propagules have been remained stable, true to type and exhibit the same characteristics as the original plant in multiple generations.

No plants of *Tiarella* 'Cutting Edge' have been sold, in this country or anywhere in the world, prior to the filing of this application, nor has any disclosure of the new plant been made prior to the filing of this application with the exception of that which was disclosed within one year of the filing of this application and was either derived directly or indirectly from the inventor.

BRIEF SUMMARY OF THE INVENTION

The nearest comparison varieties known to the applicant is the parent 'Timbuktu'. Compared with the new plant, 'Timbuktu' has more rounded and less acute lobe apices, the flower buds are not as pinkish and the habit is smaller in height and width. 'Candy Striper' U.S. Plant Pat. No. 15,528 has longer thinner lobes with less serration than the new plant. 'Crow Feathers' U.S. Plant Pat. No. 12,335 has broader lobes and less dark burgundy surrounding the veins at spring flowering than the new plant. 'Cutting Edge' is more clumping than 'Jeepers Creepers' U.S. Plant Pat. No. 13,437, and the foliage of the new plant is more dissected. 'Pacific Crest' U.S. Plant Pat. No. 23,591 has a running habit with glossy foliage surface and more rounded lobe apices. 'Pink Skyrocket' U.S. Plant Pat. No. 13,382 has deeper pink flower buds and less burgundy leaf centers at spring flowering than 'Cutting Edge'. 'Spring Symphony' U.S. Plant Pat. No. 12,397 has lighter pink flowers and leaves with thinner lobes, less serration to the margins and thinner burgundy palms in the center at flowering. 'Sugar and Spice' U.S. Plant Pat. No. 16,738 has shinier leaf surfaces with more reddish center markings at flowering and the flowers are light pink. 'Fingerpaint' U.S. Plant Pat. No. 28,012 has a more rounded and crenate lobe apices with darker and broader maroon-purple palm in the leaf center than the new plant. 'Jade Peacock' U.S. Plant Pat. No. 26,730 has broader leaf lobes and broader burgundy markings in the leaf center.

*Tiarella* 'Cutting Edge' is distinct from all other foamflower plants known to the applicant in the following combined traits:

1. Pale pink flower buds densely displayed on numerous moderately branched panicles.
2. Clumping mounded habit with numerous panicles through spring period.
3. Deeply lobed palmate foliage dissected nearly to petiole.
4. Foliage color with center burgundy palm surrounded by chartreuse to medium green.
5. Foliage with sharply toothed margins and sharply acute lobe apices.

BRIEF DESCRIPTION OF THE DRAWINGS

The drawing of *Tiarella* 'Cutting Edge' demonstrates the overall appearance of the plant including the unique traits. The colors are as accurate as reasonably possible with color reproductions. Some slight variation of color may occur as a result of lighting quality, intensity, wavelength, and direction or reflection.

The drawing shows a two-year-old specimen of the new plant growing in a shaded trial garden in Zeeland, Mich. in mid-spring while in full flower also displaying the deep burgundy leaf centers.

DETAILED BOTANICAL DESCRIPTION

The following description is based on a two-year-old plant of *Tiarella* 'Cutting Edge' growing in a partially shaded greenhouse and shaded trial garden in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female (seed parent) 'Timbuktu'; male (pollen) 'Timbuktu';

Plant habit: Hardy herbaceous perennial with clumping mounded habit with basal shoots each with a basal rosette of foliage; mounded foliage to about 22.0 cm tall, flowering to about 53.0 cm tall and about 56.0 cm in diameter; about 20 stems and 150 leaves per plant;

Roots: Fibrous, finely branched; color light beige to near white depending on soil type;

Growth rate: Rapid, rooting from cutting in 2 weeks and finishing in three-liter container in about 3 months;

Stem: About 8.0 mm across and 1.0 cm long; color nearest RHS 186A;

Foliage: Palmately-lobed, typically penta-lobed, rarely more; dissected nearly to petiole;

Leaf blade size: To about 17.0 cm long and 14.0 cm wide, average about 12.0 cm long and about 8.5 cm across; middle lobe to 13.0 cm long and 7.0 cm across, average 9.0 cm long and 4.8 cm across; middle lob with secondary lobes to 2.5 cm long and 1.0 cm wide; about seven to ten leaves per stem;

Leaf margin: Hirsutulous, margins serrate to crenate;

Leaf apex: Acute to apiculate and micro ciliolate;

Leaf base: Auriculate with lowest lobes slightly imbricate;

Leaf surface: Pubescent adaxial, puberulent abaxial; surfaces adaxial and abaxial matte;

Leaf quantity: About 100 per plant;

Leaf blade color: Seasonably slightly variable; young emerging leaves adaxial surface nearest RHS 144A with are surrounding major veins of nearest RHS N186C, abaxial nearest RHS 146D with area surrounding veins between RHS N186C and RHS 187B; mature leaves adaxial surface nearest RHS 137C with center darker burgundy surrounding veins to nearly 90 percent of the width of the center lobe and slightly less in side lobes color nearest RHS N186A, abaxial between RHS 138A and RHS 146A around margins and surrounding veins nearest RHS 146A with undertone of nearest RHS N187B; winter adaxial variable center surrounding veins nearest RHS 200B, outer portion mixture of nearest RHS 185B and between RHS 177B and RHS 176B, abaxial nearest RHS 182B;

Veins: Palmate; hirsutulous adaxial and abaxial; adaxial slightly impressed, abaxial costate;

Vein color: Young adaxial distally and toward margins nearest RHS 145C with area toward leaf center between RHS 182A and RHS 182B, young abaxial veins nearest RHS 145C; Mature adaxial veins toward center nearest RHS N186A and distally and along margins nearest RHS 137C, mature abaxial veins nearest RHS 195A;

Petiole: Terete, pubescent, wiry; outwardly; to about 17.0 cm long and 3.0 mm diameter at base, average 14.0 cm long and 2.5 mm diameter;

Petiole color: Young between RHS 146D and RHS 145A with base blushed with nearest RHS 187C; mature nearest RHS 148A with slight blush nearest RHS N186C;

Inflorescence: Compact, lightly-branched panicle; about 30 to 40 racemes per plant in mid-spring; to about 130 flowers per panicle, average about 66 flowers per main stem; upright;

Panicle branches: Pubescent; terete; in lower two to three nodes, about 15 to 30 degree angle from vertical, to about 5.3 cm long and 2.0 mm diameter; producing pubescent up to 58 flowers per branch;

Flowering period: Flowering starting about April 25$^{th}$ in Michigan for about 4 weeks;

Fragrance: Light sweet fragrance;

Peduncle: Terete, pubescent; wiry and flexible; upright; to about 53.0 cm tall and 3.0 mm in diameter; attitude upwards;

Peduncle color: Nearest RHS 148A with light blushing nearest RHS N186C;

Pedicel: Terete, pubescent, to about 5.0 mm long and 0.5 mm diameter, average about 4.5 mm long and 0.5 mm diameter;

Pedicel color: Blend between RHS 182B and RHS 186C, becoming nearest RHS 157B distally with flower maturity;

Buds: One day prior to opening — globose to ellipsoidal; glandular; about 3.5 mm long and 2.5 mm diameter; with pistil exserted to about 5.0 mm long; drooping until open;

Bud color: Apex nearest RHS N155B;

Flower: Perfect; rotate; actinomophic; about 6.0 mm long and 8.0 mm in diameter at face; individual flowers lasting about 4 days on plant or on cut panicle;

Flower density: Moderately dense, flowers about 2.3 mm apart;

Flower attitude: Outright to slightly upright;

Petals: Five; glabrous; lanceolate; margin entire, apex sharply acute, base attenuate; about 3.0 mm long and 0.5 mm wide; not persistent;

Petal color: White, nearest RHS NN155D on both surfaces;

Calyx: Five sepals; glabrous adaxial, puberulent abaxial; lanceolate; acute apex; base truncate and fused; about 5.5 mm across;

Sepal size: About 2.5 mm long and 1.0 mm wide;

Sepal color: Adaxial near white, nearest RHS N155B adaxial and abaxial when opened;

Androecium: Typically ten;

*Filaments*.—Thin, exserted, about 4.0 mm long and about 0.3 mm diameter; color white, nearest RHS NN155D.

*Anthers*.—Ellipsoidal; longitudinal, basifixed; about 0.7 mm long and 0.5 mm diameter; color nearest RHS 29B prior to dehiscing.

*Pollen*.—Abundant; color nearest RHS 28B.

Gynoecium: Carpels one; about 5.5 mm long;

*Style*.—Two, separate; about 2.5 mm long and about 2.5 mm across; color nearest RHS NN155D.

*Stigma*.—Globose; less than 0.3 mm diameter; color nearest RHS NN155D.

*Ovary*.—Oblong with pointed apex; about 2.5 mm long and 2.5 mm diameter; color nearest RHS NN155D becoming pale green nearest RHS 157D.

*Fruit*.—Two-valved capsule, about 8.0 mm long and 2.0 mm in diameter at widest portion; color beginning nearest RHS 145C, drying to nearest RHS 199A.

Seed: Ellipsoid; shiny; to 1.0 mm long and 0.5 mm wide; typically two per fruit; color nearest RHS 202A;

Disease and pest tolerance: The new plant grows best with ample moisture, good drainage and some shade. Not typically browsed by deer. Cold hardy and heat tolerant from USDA zones 4 to 9. Other resistance and tolerance beyond that normal for foam flower has not been observed.

I claim:

1. The new and distinct foamflower plant named *Tiarella* 'Cutting Edge' as herein described and illustrated.

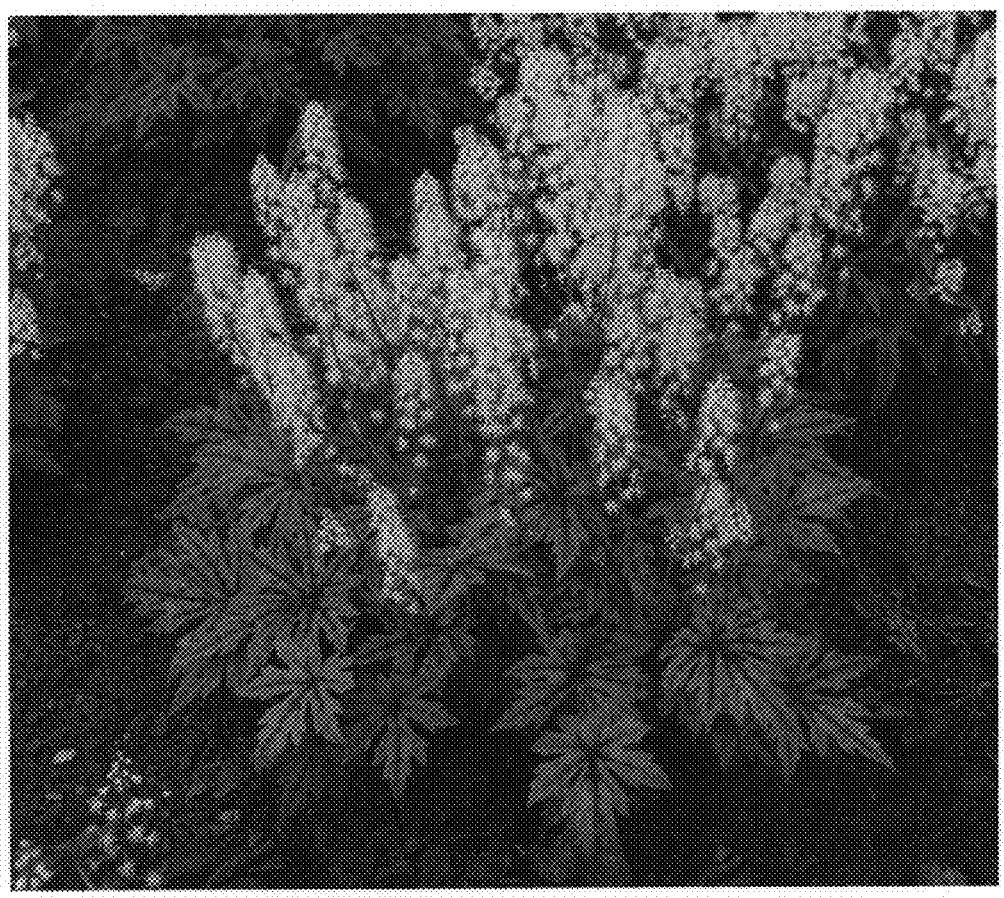

* * * * *